US006670521B2

(12) United States Patent
Noda et al.

(10) Patent No.: US 6,670,521 B2
(45) Date of Patent: Dec. 30, 2003

(54) DISPERSIBLE ABSORBENT PRODUCTS AND METHODS OF MANUFACTURE AND USE

(75) Inventors: Isao Noda, Fairfield, OH (US); Sarah Beth Gross, Cincinnati, OH (US); Hugh Joseph O'Donnell, Cincinnati, OH (US); James Cameron Horney, Cincinnati, OH (US); Mark Dawson Midkiff, Fairfield, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 16 days.

(21) Appl. No.: 09/838,779

(22) Filed: Apr. 20, 2001

(65) Prior Publication Data

US 2001/0051796 A1 Dec. 13, 2001

Related U.S. Application Data

(63) Continuation-in-part of application No. 09/711,475, filed on Nov. 13, 2000, which is a continuation-in-part of application No. 09/553,698, filed on Apr. 20, 2000, now abandoned.

(51) Int. Cl.⁷ .............................. A61F 13/15; B32B 5/14
(52) U.S. Cl. ......................... 604/364; 442/58; 442/153
(58) Field of Search ........................ 604/364, 374, 604/383; 442/43, 44, 58, 93, 96, 97, 103, 118, 153, 164

(56) References Cited

U.S. PATENT DOCUMENTS

| | | | |
|---|---|---|---|
| 3,521,638 A | | 7/1970 | Parrish |
| 3,563,241 A | * | 2/1971 | Evans et al. ............... 160/169 |
| 3,665,923 A | * | 5/1972 | Champaign, Jr. ........... 604/364 |
| 3,798,120 A | | 3/1974 | Enloe et al. |
| 3,881,210 A | | 5/1975 | Drach et al. |
| 3,923,592 A | | 12/1975 | George et al. |
| 3,939,836 A | * | 2/1976 | Tunc ............................ 428/198 |
| 4,002,171 A | * | 1/1977 | Taft ............................. 604/364 |
| 4,107,364 A | | 8/1978 | Sisson |
| 4,117,187 A | * | 9/1978 | Adams et al. ............... 442/118 |
| 4,186,233 A | | 1/1980 | Krajewski et al. |
| 4,258,849 A | | 3/1981 | Miller |

(List continued on next page.)

FOREIGN PATENT DOCUMENTS

| | | |
|---|---|---|
| EP | 0 896089 A1 | 2/1998 |
| FR | 2 672 788 A1 | 8/1992 |
| GB | 1 236 904 | 6/1971 |
| GB | 1441690 | 7/1976 |
| GB | 2281081 A | 2/1995 |
| JP | 54-015983 | 2/1979 |
| JP | 03-180600 | 8/1991 |
| JP | 06-042897 B2 | 6/1994 |
| JP | 10-014807 | 1/1998 |
| JP | 10-099248 | 4/1998 |
| JP | 10-099249 | 4/1998 |
| WO | WO 96/16217 A2 | 5/1996 |
| WO | WO 99/08727 | 2/1999 |
| WO | WO 99/26672 | 6/1999 |
| WO | WO 99/33648 | 7/1999 |
| WO | WO 99/42068 A1 | 8/1999 |
| WO | WO 00/38750 | 7/2000 |
| WO | WO 00/39378 | 7/2000 |
| WO | WO 01/80800 A1 | 11/2001 |

*Primary Examiner*—Weilun Lo
*Assistant Examiner*—Jamisue A Webb
(74) *Attorney, Agent, or Firm*—Caroline Wei-Berk; Dara M. Kendall; Angela Marie Stone (57) ABSTRACT

A dispersible absorbent product comprises a mechanically weakened fibrous web. The dispersible absorbent product can absorb a sufficient amount of fluid without becoming overloaded and suffering from leakage, and is dispersible using a standard toilet. The mechanically weakened regions of the web enhance the dispersibility of the product. Additionally, the dispersible absorbent products may be pre-moistened with a composition. The pre-moistened products are stable in storage, easily dispersible down a toilet, and deliver cleaning, conditioning, and like benefits. Methods of making such dispersible absorbent products are also disclosed.

33 Claims, 5 Drawing Sheets

U.S. PATENT DOCUMENTS

| | | | | |
|---|---|---|---|---|
| 4,275,105 A | * | 6/1981 | Boyd et al. | 428/198 |
| 4,419,403 A | * | 12/1983 | Varona | 442/153 |
| 4,575,891 A | | 3/1986 | Valente | |
| 4,734,941 A | | 4/1988 | DeWitt et al. | |
| 4,897,301 A | * | 1/1990 | Uno et al. | 428/209 |
| 4,944,734 A | * | 7/1990 | Wallach | 604/358 |
| 5,143,679 A | | 9/1992 | Weber et al. | |
| 5,156,793 A | | 10/1992 | Buell et al. | |
| 5,167,897 A | | 12/1992 | Weber et al. | |
| 5,300,358 A | * | 4/1994 | Evers | 428/422 |
| 5,384,189 A | * | 1/1995 | Kuroda et al. | 428/369 |
| 5,498,470 A | | 3/1996 | McLean et al. | |
| 5,506,041 A | * | 4/1996 | Tanaka et al. | 15/209.1 |
| 5,509,913 A | | 4/1996 | Yeo | |
| 5,629,081 A | * | 5/1997 | Richards et al. | 442/96 |
| 5,650,214 A | | 7/1997 | Anderson et al. | |
| 5,885,265 A | * | 3/1999 | Osborn et al. | 604/367 |
| 5,986,165 A | * | 11/1999 | Moder et al. | 132/286 |
| 6,114,263 A | | 9/2000 | Benson et al. | |
| 6,121,170 A | | 9/2000 | Tsai et al. | |
| 6,203,654 B1 | * | 3/2001 | McFall et al. | 156/201 |
| 6,384,297 B1 | * | 5/2002 | Colman et al. | 604/364 |
| 6,420,013 B1 | * | 7/2002 | Vinson et al. | 428/154 |
| 6,548,427 B1 | * | 4/2003 | Shannon et al. | 442/118 |

* cited by examiner

DISPERSIBLE ABSORBENT PRODUCTS AND METHODS OF MANUFACTURE AND USE

This application is a continuation-in-part application of U.S. application Ser. No. 09/711,475, filed Nov. 13, 2000, in the name of Horney et al., which is a continuation-in-part application of U.S. application Ser. No. 09/553,698, filed Apr. 20, 2000 now abandoned, in the name of Horney et al.

FIELD OF INVENTION

This invention is directed toward rapidly dispersible absorbent products and methods for making and using such products. This invention is especially directed toward rapidly dispersible absorbent products that are flushable down a standard toilet system.

BACKGROUND OF THE INVENTION

Disposable absorbent articles such as feminine hygiene products, diapers, training pants, adult incontinence products, offer great convenience and are widely used by consumers. However, the popularity of these products has created a need regarding their disposal. Typical disposal methods such as incineration or landfill are generally considered unsatisfactory because of cost and environmental concerns. An alternative disposal method has been in practice, which involves flushing the article down the conventional toilet, subsequently, degrading it in the municipal or private sewage system or septic system. This disposal method is generally considered convenient and discrete. For this disposal method, the suitable materials should not only maintain its structural integrity for the intended use but also disintegrate readily such that the material can be flushed down the conventional toilet and plumbing system without creating blockage. These materials requirements become more challenging in the pre-moistened applications where the materials need to have storage stability for a long period of time in a wet condition. Additionally, the suitable materials are preferably biodegradable such that there is no accumulation of large chunks of the materials in the waste handling system.

Numerous approaches have been tried to provide flushable fibrous products for use in a variety of uses including, but not necessarily limited to, sanitary napkins, diapers, toilet seat wipes, and the like. For example: U.S. Pat. No. 5,300,358 issued Apr. 5, 1994 to Evers discloses a degradable and flushable absorbent structure for sanitary napkins, diapers, and the like having an absorbent fibrous core and a backsheet comprising a cold water soluble material; U.S. Pat. No. 4,575,891 issued Mar. 18, 1986 to M. Valente discloses a small flushable toilet seat wipe of approximately 2 inches by 2 inches having a cardboard upper layer; GB Patent Publication 2,281,081, published Feb. 22, 1995 by R. L. Lewis et al. discloses a web of fibrous material and polymeric binder which is said to be sufficiently hydro-disintegratable to be flushed down a toilet. The binder is applied by spraying or dipping onto wet-laid or air-laid webs. EP patent Publication 896,089 A1 published Feb. 10, 1999 by Taakeuchi et al. discloses a fibrous sheet that is disintegratable when immersed in large amounts of water comprising a fibrous sheet treated with a binder such as polyvinyl alcohol. U.S. Pat. No. 4,734,941 issued Apr. 5, 1988 to De Witt et al. discloses a flushable urine-conducting product for positioning between the legs of a female to direct urine to a receptacle. The product comprises a fibrous or non-fibrous sheet that is disintegratable in water and a water soluble polymer film. The preferred disintegratable sheet is tissue paper. U.S. Pat. No. 5,509,913 issued Apr. 23, 1996 to Yeo discloses a toilet flushable product such as diapers, fabrics, and sheets for use as wipes that are insoluble in the presence of body waste fluid but soluble in the presence of normal tap water.

There is a need for a convenient, easy-to-use, and easy to dispose of absorbent product which effectively cleans or absorbs residual body exudates, and then can be readily disposed of in any toilet and subsequent waste handling system (e.g., sewer, septic tank). Therefore, it is desirable to provide absorbent products useful for absorption of residual body exudates that are sufficiently dispersible such that they can be easily flushed down toilets and passes readily through plumbing.

It is further desirable to provide degradable products such that they do not accumulate substantially in the sewer, septic tank, or other waste handling systems.

It is also desirable to provide pre-moistened products that are stable in storage, dispersible in the toilet/disposal system, and degradable in the sewer, septic, or other waste handling system.

It is also desirable to provide for a mechanically weakened web such that it breaks up and is dispersible during disposal yet retains sufficient integrity that it does not break up during use.

It is further desirable to provide products pre-moistened with a liquid or a composition such that they deliver hard surface cleaning, skin cleaning, skin conditioning and/or other skin benefits.

These and other needs addresses by the invention as hereinafter described may become apparent to one of ordinary skill in the art are intended to be encompassed by the present invention in accordance with the claims which follow.

SUMMARY OF THE INVENTION

The present invention provides dispersible absorbent products comprising a mechanically weakened fibrous web. The dispersible absorbent products can absorb a sufficient amount of fluid without becoming overloaded and suffering from leakage, and can be easily disposed using a standard toilet. The mechanically weakened regions of the web enhance the dispersibility of the product. Additionally, the dispersible absorbent products may be pre-moistened with a composition suitable for delivering hard surface cleaning or polishing, household cleaning or polishing, skin cleansing, skin conditioning, and like cleaning, conditioning, polishing benefits. The pre-moistened products are stable in storage and dispersible in a standard toilet. This invention further provides methods of making such dispersible absorbent products by mechanically weakening a fibrous web.

DETAILED DESCRIPTION OF THE INVENTION

"Dispersible" as used herein means the product exhibits visible changes after being flushed down a standard toilet; the changes may include any visible failures to the integrity of the product, such as holes, slits, shreds; breaking apart into smaller sections; dissolving; or a combination thereof. Typically, a product is dispersible if it has a score of at least 2 in the Flush Dispersibility Test disclosed below.

"Flushable" as used herein means discardable in a toilet, urinal, or other flushing device made for the purpose of receiving urine or other bodily exudates and transporting it through a plumbing system by hydraulic pressure to a sewage system. "Water-Responsive" as used herein a material or an article made thereof (such as film, fiber nonwoven, laminate, shaped article) is capable of being weakened, broken into pieces, or dissolved when immersed in an aqueous medium.

"Comprising" means the various components such as the films, layers, polymers, and materials, used in the present invention can be employed in various combinations and with other optional components, and that the various steps used in the present invention can be used in various orders or combinations, so long as the objectives of the present invention are achieved. Accordingly, the term "comprising" encompasses the more restrictive terms "consisting essentially of" and "consisting of".

The present invention provides dispersible absorbent products that be can easily and quickly disperse and are highly absorbent.

The preferred dispersible absorbent product will be in the form of a sheet. Such sheet can be of an appropriate and convenient size for storage before use, absorption of the residual urine or other intended volume of fluid, discreteness for storage and use, and ease of disposal after use. Such sheet preferably has a top planar surface area of from about 10 $cm^2$ to about 1000 $cm^2$, more preferably from about 20 $cm^2$ to about 500 $cm^2$, most preferably from about 25 $cm^2$ to about 250 $cm^2$.

The sheets can have any number of shapes including but not limited to squares, rectangles, triangles, polygonals, circles, ovals, or other curvilinear shapes. The sheets can also be provided in the form a large sheet or roll having lines of weakness or perforations included that facilitate dividing the sheet into a plurality of smaller sheets of sizes preferably within the ranges set forth above.

The thickness of the sheet can vary widely depending upon materials used, absorptive properties, basis weight, density, and construction, as well as intended use. In general, sheets intended for absorbing residual urine or cleaning residual feces or menses will preferably have a thickness of from about 0.3 mm to about 5 mm, preferably from about 0.5 mm to about 2.5 mm, more preferably from about 0.75 mm to about 2.2 mm, most preferably from about 0.8 mm to about 2 mm.

The absorbent products of the present invention preferably have a basis weight of from about 30 $g/m^2$ to about 250 $g/m^2$, more preferably from about 40 $g/m^2$ to about 150 $g/m^2$, most preferably from about 50 $g/m^2$ to about 120 $g/m^2$. Higher or lower basis weights are not necessarily meant to be excluded, and may be desirable depending upon the intended use of the products and the means by which the product is intended to be disposed of after use.

The dispersible absorbent products hereof can also be of shapes other than sheets including without limitation three dimensional shapes such as cubes, other polygonal shapes (e.g., with four or more sides), rounded or ovalized geometric shapes (e.g., balls, wads, cylinders), etc. Such products preferably have total exterior surface areas of from about 10 $cm^2$ to about 1000 $cm^2$, more preferably from about 20 $cm^2$ to about 500 $cm^2$.

It is a beneficial feature of disposable products that disposal of the products does not cause clogging of the flushing devices or like disposal devices. This is particularly important in public lavatories that experience high levels of use and/or where easily cloggable flushing devices are used. The dispersible absorbent products according to the present invention therefore are highly dispersible in a Flush Dispersibility Test, which simulates the disposal conditions the products experience in a lavatory. The Flush Dispersibility Test (FDT) is disclosed below in the Test Methods below. The dispersible absorbent products of the present invention have a FDT score of at least 2.

In another aspect, the dispersible absorbent products of the present invention preferably have a "Rate of Dispersibility", as determined according the Rate of Dispersibility Test described below in the Test Methods section, of 200 seconds or less, more preferably 120 seconds or less, more preferably 90 seconds or less, more preferably 60 seconds or less, and most preferably 30 seconds or less.

The products of the present invention retain sufficient cohesiveness during use so as not to prematurely disperse or otherwise lose integrity during manufacture, storage, dispensing, or use prior to disposal in the intended receptacle. Thus, the products of the present invention will typically have a rate of Dispersibility of 5 seconds or greater. In addition to being highly dispersible, the dispersed products should be capable of flowing through the orifices they will be flushed through subsequent to use.

With respect to dispersible absorbent products made from fibrous material or other nondissolvable material, for example, the product should disperse into individual fibers or into discrete flushable sections of fibers, with such sections still retaining cohesiveness but being sufficiently small and/or conformable to pass through small orifices. As used herein, "sections" of fibers can include uniformly (for example, but not limited to, squares) or non-uniformly (for example, but not limited to, chunks, agglomerations, etc.) shaped sections of fibers. Aqueous slurries of fibers shall be considered as containing a plurality of individualized fibers or sections of fibers, as the case may be. Fibers may be longer in length than the orifices and still be flushable so long as they are sufficiently dispersed from one another that they retain sufficient flexibility to fit through the orifices under the pressures conventionally experienced during flushing and do not block or clog the orifices. Nonfibrous materials that disperse into discrete sections rather than dissolving should be small or flexible enough to fit through the dimensions of the orifices.

The dispersible absorbent products of the present invention must flow through the orifice within the disposal or plumbing system in order to be flushed into a septic, sewer, or other waste handling system. Materials that are used in the present invention preferably, but not required to, dissolve or disperse into sections that have a cross-section that that are slightly smaller than the size of the orifice through which it must pass. The typical size of the orifice in the disposal device or plumbing system is about 2" (5 cm) diameter. Thus, the dispersible absorbent product sections preferably have cross sections can be enclosed by a rectangle having a maximum side length of about 5 cm or less, more preferably about 4 cm or less, more preferably about 3 cm or less, more preferably about 2.5 cm or less. Alternatively, a larger size product made of flexible materials may also passes through the orifices within the disposal or plumbing system under the pressure/vortex typically experienced during flushing. Moreover, the product may develop visible failures in its structural integrity, such as holes, slits, shreds, or may break down into smaller sections, which facilitates further breakdown in the sewer, septic or other waste handling systems.

The dispersible absorbent products of the present invention can quickly absorb fluid deposited onto the surface of the products. Furthermore, in many circumstances, the products hereof will be used under circumstances wherein fluid will contact the dispersible absorbent product at an angle diverging from the horizontal. Therefore the preferred dispersible absorbent product of the present invention quickly absorb the fluid coming into contact with it without unabsorbed fluid running down the surface of the product. As is well known and understood in the art, total absorption capability is dependent upon the choice of structural materials (chemistry and shape of the material and topography of the material surface), contact angle of fluid on the absorbent structure surface, and pore volume distribution of the structure. Capillary or hydrostatic pressure of the products can be enhanced by methods well known in the art such as, but not limited to, surface treatments of the absorbent element, adjusting pore size, density, and fiber length in absorbent elements. Products used for purposes such as absorbing residual urine or other fluids preferably should have an absorptive capacity sufficient to absorb the amount of fluids for its intended use. In general, the dispersible absorbent product intended for use to absorb residual urine or other fluids preferably should be able to absorb at least 0.2 ml of fluids, more preferably at least 0.5 ml, even more preferably at least 0.7 ml, most preferably at least about 1.0 ml.

The mechanical weakening processes described below provided the dispersible absorbent products of the present invention with a textured surface. Such textured surface provides softness and a cloth-like feel to the product. Further, the textured surface contains lofts and interstitial voids, which enhance the absorbency or liquid holding capacity of the product. Additionally, the surface texture also provides a plurality of regional contacts with the target surface, thus, improves the cleaning effectiveness of the product.

The dispersible absorbent products of the present invention may be pre-moistened with a composition. The composition may be a simple liquid, such as water, lower alcohols including methanol, ethanol, propanol, mineral oil, and the like. The composition may be any composition generally known to one skilled in the art as being suitable for the intended use such as cleaning, conditioning, polishing, and the like, and is disclosed in more details below.

The liquid loading level of the pre-moistened product ranges from about 50 wt % to about 500 wt %, preferably from about 75 wt % to about 400 wt %, and more preferably from about 100 wt % to about 300 wt %, based on the dry weight of the product. Typically, a web loses some or all of its surface texture when loaded with a liquid or a composition. It is surprising to find that the pre-moistened product of the present invention substantially retains its surface texture, especially when the surface texture is produced by the selfing process described below. Thus, the pre-moistened products retain the desirable soft, cloth-like feel as well as the liquid holding capacity of the dry products.

Since pre-moistened products are often stored for a long period of time, from about six months to three years, the pre-moistened products need to retain sufficient structural integrity until use. It is known that the inclusion of a large percentage of wet strength resin (e.g., melamine resins, urea formaldehyde resins) can improve the shelf life of pre-moistened wipes. However, the resultant products have such a high wet strength such that they are not easily Dispersible under the pressure/vortex typically experienced in a flushing disposal device.

It is surprising to find that the pre-moistened products of the present invention may be substantially free of wet strength resins or binders and still achieve dispersibility and a long shelf life, up to about three years. For example, a mechanically weakened, fibrous web of the present invention, which comprises at least 50 wt % rayon, will retain its structural integrity up to about 3 years, when pre-moistened with water. In another embodiment, the dispersible absorbent product is made of 100 wt % rayon (i.e., without any wet strength resin), the product, pre-moistened with water, is stable in storage for three years or longer. Despite of the storage stability in a pre-moistened condition, the mechanically weakened web has sufficiently weakened regions such that the pressure/vortex typically provided by a disposal device is sufficient to render the web dispersible in flushing.

Incorporation of the wet strength resins or binders may enhance the break down of the product subsequent to flushing down the toilet. Thus, less than about 5 wt % wet strength resins or binders may optionally be added to the dispersible absorbent product of the present invention, preferably less than 3 wt %, more preferably less than 1 wt %, and most preferably less than 0.5 wt %. Since the dispersibility of the product of the present invention relies primarily on the mechanical weakening of the structure, higher level of wet strength resins or binders may be included in the product and still achieve a dispersible product.

Optional binders may include, but not limited to, water-soluble polymers such as polyalkylene oxides including polyethylene oxide, poly(ethylene/propylene) oxide; polyvinyl alcohol; vinyl alcohol copolymers; starch; and polyelectrolytes having polar or ionic functional groups pendent from a polymeric backbone chain, wherein the functional groups typically include sulfonic, carboxylic, acrylic, methacrylic and mixtures thereof, and the polymeric backbone chains typically include polyesters, polyacrylamides, vinyl polymers, acrylic polymers, methacrylic polymers, and copolymers thereof. These and other binders are generally known to one of ordinary skill in the art. The mechanical weakening sufficient to render the product dispersible generally resulting in a significant reduction in the tensile strength of the web. Typically, a reduction of about 90%, preferably of about 80%, more preferably of about 70%, and most preferably of about 50%, based on the tensile strength of the unweakened web, is sufficient to render the resulting product dispersible.

However, the mechanical weakened product must retain sufficient structural integrity for the intended use. Thus, the mechanically weakened product should desirably have a residual (i.e., after the mechanical weakening process) tensile strength of at least about 70 g/in (28 g/cm), preferably at least about 150 g/in (60 g/cm), more preferably at least about 250 g/in (100 g/cm), and most preferably at least about 500 g/in (200 g/cm).

The dispersible absorbent products of the present invention can be made from any material capable of absorbing fluids, such as urine and other aqueous fluids. These include natural and synthetic fibers, foams, sponges, natural absorbent materials such as peat, and absorbent porous polymeric macrostructures comprising inter-particle cross-linked aggregate. Preferred materials include fibers and foams. Suitable synthetic fibers include fibers made from polypropylene, polyethylene, and polyester, polyacrylates, and copolymers thereof and mixtures thereof. Derivatives, homologs, and analogs thereof are meant to be included in the above materials. Co-form fibers such as those with a sheath and core construction of separate polymeric materials, or of a bias construction with two separate materials are also meant to be included. Fibers that are hydrophobic may be treated with wetting agents in order to facilitate absorption of aqueous liquids. Capillary channel fibers may also be used. Capillary channel fibers are fibers having internal or external capillary channels that facilitate wicking of fluids. Capillary channel fibers are disclosed, for example, in U.S. Pat. No. 5,200,248 issued Apr. 6, 1993 to Thompson et al., incorporated herein by reference.

The product of the present invention can be a fibrous web or a polymeric film, preferably a fibrous web. The fibrous webs can be woven or nonwoven, preferably nonwoven. Nonwoven web structures can be air laid, wet laid or carded. The air laid processes are preferred for long fibers and/or hydrophilic fibers such as rayon fibers, which have a tendency to agglomerate in the wet laid process. The air laid web is typically hydroentangled to set the structure. Though other bonding methods known in the art may also be used for making the fibrous webs useful herein. The nonwoven webs suitable for use in the present invention typically comprise a high proportion of staple length or longer fibers, typically at least about 75%, preferably at least about 85%, and more preferably at least about 95%, by the weight of the web. The average fiber length is at least about 1 cm, preferably at least about 2 cm, and most preferably at least about 3 cm.

The nonwoven webs are mechanically weakened by application of structural weakening processes such as cutting, slitting, perforating, tentering, tensioning, ring rolling and its variants, as further described below.

Water-insoluble, biodegradable polymers useful in the present invention include poly (lactic acid) polymers and blends thereof, disclosed in U.S. Pat. No. 5,698,322 (Tsai et al.) issued Dec. 16, 1997, U.S. Pat. No. 5,760,144 (Ozcki et al.) issued Jun. 2, 1998, U.S. Pat. No. 5,910,545 (Tsai et al.) issued Jun. 8, 1998, U.S. Pat. No. 5,945,480 (Wang et al.) issued Aug. 31, 1999, PCT Publication WO 98/29493 (Tsai et al.) published Jul. 9, 1998, PCT Publication WO 00/43579 (Lindquist et al.) published Jul. 27, 2000 (all are herein incorporated by reference); polycaprolactones disclosed in U.S. Pat. No. 5,391,423 (Wnuk et al), issued Feb. 21, 1995 (herein incorporated by reference); aliphatic polyesters; aliphatic polyalkylene succinate polymers, polyalkylene succinate adipate copolymers or mixtures thereof disclosed in U.S. Pat. No. 5,849,401 (El-Afandi et al), issued Dec. 15, 1998 and U.S. Pat. No. 5,910,545 (Tsai et al), issued Jun. 8, 1999 (herein incorporated by reference); aliphatic-aromatic copolyesters disclosed in U.S. Pat. No. 5,292,783 (Buchanan et al), issued Mar. 8, 1994, U.S. Pat. No. 5,446,079 (Buchanan et al), issued Aug. 29, 1995, U.S. Pat. No. 5,559,858 (Buchanan et al), issued Feb. 4, 1997, and U.S. Pat. No. 5,580,911 (Buchanan et al), issued Dec. 3, 1996 (herein incorporated by reference); polyesteramides including aliphatic and partially aromatic polyesteramides disclosed in U.S. Pat. No. 5,644,020 (Timmerman et al.), issued Jul. 1, 1997 (herein incorporated by reference); and polyhydroxyalkoates and copolymers including polyhydroxy butyrates and polyhydroxy butyrate/valerate copolymers disclosed in U.S. Pat. No. 5,489,470 (Noda) issued on Feb. 6, 1996 and U.S. Pat. No. 5,498,692 (Noda) issued on Mar. 12, 1996 (both are herein incorporated by reference).

Suitable water-insoluble, biodegradable polymers that are commercially available include polybutylene succinate polymers and polybutylene succinate adipate copolymers are available from Showa Highpolymer Co. Ltd, Tokyo, Japan, under the Bionolle® Type 1000 and 3000 designations; poly(tetramethylene) adipate-co-terephthalate copolyesters available from Eastman Chemical under the Eastar® Biodegradable Copolyester 14776 designation; and aliphatic polesteramides available from Bayer under the BAK® trade designation.

Water-responsive polymers useful in the present invention may include water-soluble polymers. As used herein, the term "water-soluble" means a polymer or an article made thereof (such as fiber, film, nonwoven, laminate, shaped article) is completely or substantially solubilized, dissolved or dispersed when exposed to an aqueous environment. When water-soluble polymers are incorporated into the absorbent dispersible products of the present invention, their levels are controlled to provide for storage stability (in the case of the pre-moistened products), and to prevent break-up of the product in use (in the case of the dry products). Therefore, the weight percent of water-soluble polymer in the products of the present invention is preferably no greater than about 50%, more preferably no greater than about 30%, even more preferably no greater than about 15%, and most preferably no greater than about 5%.

Nonlimiting examples of water-soluble polymers include cellulose derivatives such as hydroxyalkyl cellulose, particularly hydroxypropyl cellulose, alkyl hydroxypropyl cellulose; polyalkylene oxides such as polyethylene oxide, polypropylene oxide, poly(ethylene-propylene) oxide; polyvinyl alcohol and polyvinyl alcohol copolymers; other vinyl polymers such as polyvinylpyrolidone, polyvinyl pyridine; starch such as gelatinized starch, and interpenetrated networks of starch with ethylene/vinyl alcohol copolymers disclosed in U.S. Pat. No. 5,391,423 (Wnuk et al), issued Feb. 21, 1995 (herein incorporated by reference); nylon copolymers; acrylic acid copolymers; polyethylene glycol; as well as compatible mixtures and blends of these polymers.

Suitable, commercially available water-soluble polymers include polyethylene oxide available from Union Carbide under the designation Polyox® WSRN-10 (Mw 100,000), WSRN-80 (Mw 200,000) and WSRN-750 (Mw 300,000), and polyvinyl alcohol available from Air Products under the designation Vinex® 1090, 2034, 2025, 2144 and 5030.

Water-responsive polymers useful in the present invention may also include a variety of biodegradable polymers, which have limited to zero solubility in water. As used herein, "biodegradable" means a polymer, layer, film or material that is capable of being degraded completely or substantially completely into carbon dioxide, methane, water, biomass and inorganic materials by or in the presence of microorganisms. The biodegradation potential can be estimated by measuring carbon dioxide evolution and dissolved organic carbon removal from a medium containing the substance being tested as the sole carbon and energy source and a dilute bacterial inoculum obtained from the supernatant of homogenized activated sludge. See Larson, "Estimation of Biodegradation Potential of Xenobiotic Organic Chemicals," *Applied and Environmental Microbiology*, Volume 38 (1979), pages 1153–61, which describes a suitable method for estimating biodegradability. These polymers are primarily degradable in an aerobic environment. Although not required, anaerobically degradability of these polymers is also desirable.

In a preferred embodiment, water-insoluble polymer fibers such as rayon are used as the main component of the dispersible absorbent product of the present invention. Such products provide enhanced softness. Specifically, the product contains water-insoluble polymer fibers from at least about 50%, preferably at least about 70%, more preferably at least about 80%, more preferably at least about 90%, more preferably at least about 95%, and most preferably 100% by the dry weight of the dispersible absorbent product. When water-responsive polymer fibers are used, the dispersible absorbent product may contain water-responsive polymer fibers from about 5% to about 50%, by dry weight of the dispersible absorbent product, more preferably from about 10% to about 40%, most preferably from about 15% to about 25% by the dry weight of the dispersible product.

When the dispersible absorbent product is intended for a dry (i.e., not pre-moistened) application, the product may contain a higher amount of water-responsive polymers. A water-responsible polymer content of about 60%, preferably about 75%, more preferably about –85% of the dry weight of the product may be satisfactory.

In another embodiment, cellulosic fibers comprises from about 50% to 100% of the dry weight of the product. Cellulosic fibers include those natural fiber derived from trees or vegetations (e.g., hardwood fibers, softwood fibers, hemp, cotton, and the like), their processed/regenerated fibers (e.g., rayon) or chemically derivatized fibers (e.g., cellulose esters), and combinations thereof. Suitable hardwood fibers include eucalyptus fibers. Suitable hardwood fibers may be prepared by kraft or other chemical pulping methods. Suitable softwood fibers include southern softwood (SS) fibers and northern softwood (NS) fibers. Softwood fibers for use herein can be chemically (e.g., without limitation, kraft pulp) or mechanically pulped (e.g., without limitation, chemithermal mechanical pulp (CTMP) and thermal mechanical pulp (TMP)). Preferred softwood fibers include chemically pulped SS fibers, such as southern softwood kraft (SSK), and mechanically pulped NS fibers, such as northern softwood chemithermal mechanical pulp (CTMP) and thermal mechanical pulp (TMP).

The dispersible absorbent products of the present invention rely at least partially on the tensile strength of the web structure for product integrity during manufacture or use, it is preferred that short length fibers (e.g., pulp fibers having average fiber length of about 7 mm or less) be limited to less than about 40%, preferably less than about 25%, more preferably less than about 10%, based on the dry weight of the product.

Shorter length fibers, such as the hardwood fibers, may provide improved dispersibility and flushability of the dispersible absorbent products. Softwood fibers tend to be longer than hardwood, and can enhance tensile strength and product integrity, as well as provide better softness and greater absorbent capacity than hardwood fibers. Average fiber length for the wood pulp fibers may be determined on a number average basis, such as measured by a Kajaani FS-200 Fiber Analyzer (available from Valmet, Norcross, Ga., USA) or equivalent.

When combinations of hardwood and softwood fibers are used, the dispersible absorbent product of the present invention will preferably contains from about 5% to about 75%, by dry weight of the product, hardwood fibers, more preferably from about 5% to about 50%, most preferably from about 10% to about 20%, and from about 25% to about 95%, by dry weight of the product softwood fibers, more preferably from about 50% to about 95%, most preferably from about 80% to about 90%. Also preferably the absorbent structure comprises a mixture of SSK and northern softwood (NS) fibers (CTMP or TMP, preferably CTMP). Preferably the absorbent structure comprises from about 5% to about 75%, by dry weight of the product, northern softwood (CTMP or TMP), more preferably from about 5% to about 50%, most preferably from about 15% to about 40%, and from about 20% to about 85% southern softwood fibers, more preferably from about 45% to about 85%. An especially preferred blend contains about 15% hardwood, about 40% NS CTMP, and about 45% SSK.

The absorbent structure can also comprise an absorbent foam. Absorbent foams suitable for use in the present invention are described in: U.S. Pat. No. 5,260,345 issued to DesMarais, et al. on Nov. 9, 1993; U.S. Pat. No. 5,268,224 issued to DesMarais et al. on Dec. 7, 1993; U.S. Pat. No. 5,387,207 issued to Dyer et al. on Feb. 7, 1995; U.S. Pat. No. 5,550,167 issued to DesMarais on Aug. 27, 1996; U.S. Pat. No. 5,563,179 issued to Stone, et al. on Oct. 8, 1996; U.S. Pat. No. 5,650,222 issued to DesMarais et al. on Jul. 22, 1997; and U.S. Pat. No. 5,649,920 issued to Dyer et al. on Jul. 22, 1997; all being hereby incorporated by reference.

Porous absorbent polymeric macrostructures comprising inter-particle cross-linked aggregate are described in: U.S. Pat. No. 5,124,188 issued to Roe et al. on Jun. 23, 1992; U.S. Pat. No. 5,180,622 issued to Berg et al. on Jan. 19, 1993; and U.S. Pat. No. 5,330,822 issued to Berg et al. on Jul. 19, 1994; all incorporated herein by reference.

As described above, dispersible absorbent products of the present invention should have sufficient dispersibility characteristics in order to easily disperse upon disposal, especially in aqueous conditions. However most absorbent structures having good absorption characteristics will not be sufficiently dispersible for purposes of this invention, which requires an FDT score of at least 2. For example, commercially available toilet papers such as Charmin® (available from The Procter & Gamble Company, Cincinnati, Ohio) or Cottonelle® (available from Kimberly-Clark Corp, Neenah, Wis.) have FTD scores of 0.

Improved dispersibility can be achieved by a variety of techniques. Without limitation, these include a variety of techniques for mechanically weakening the dispersible absorbent product, such as by partially disentangling fibers of an absorbent fibrous web, and/or by incorporation into the absorbent structure of regions of weakness. Regions of weakness include but are not limited to continuous regions of weakness and discontinuous regions of weakness (including but not limited to random or patterned regions of weakness separated by a continuous region having greater tensile strength than the regions of weakness). Continuous regions of weakness include, but are not limited to, slits and linear regions (or "lines") of stretched or partially disentangled regions of the absorbent structure or fibers within the absorbent structure. Discontinuous regions of weakness include but are not limited to slits and perforations, as well as regions of stretched or lower density absorbent structure, or partially separated fibers, surrounded by higher density regions the absorbent structure. As used herein, "discrete sections" of the absorbent structure refers to sections of absorbent structure that are separated from adjacent discrete sections by regions of weakness.

In one embodiment, the discrete sections of absorbent structure are separated by regions of weakness that extend through the entire thickness of the web, such that elements of the absorbent structure do not bridge the gap between adjacent sections. In another embodiment, the regions of weakness are cuts or slits extending partially through the thickness of the absorbent structure. In yet another embodiment the regions of weakness are low density regions of weakness wherein fibers bridge the gap across the line of weakness between adjacent sections, albeit at lower density than the adjacent sections. In another embodiment the regions of weakness are regions of partially disentangled fibers. Fibrous webs, especially nonwoven webs, can be mechanically weakened by partially disentangling fibers. This can be done either throughout the entire web, or through portions of the web while retaining portions of non-disentangled fibers.

Partial disentanglement of web material fibers can be accomplished by any methods as may be known in the art, preferably but not limited to passing the web through a nip between grooved or patterned rolls—a process which has been described as pre-corrugating or "ring-rolling", such as described in U.S. Pat. No. 4,107,364 issued to Sisson on Aug. 15, 1978; U.S. Pat. No. 5,143,679 issued to G. M. Weber et al. on Sep. 1, 1972; U.S. Pat. No. 5,156,793 issued to K. B. Buell et al. on Oct. 20, 1992; and U.S. Pat. No. 5,167,897 issued to G. M. Weber et al. on Dec. 1, 1992; all incorporated herein by reference. Modified ring rolling methods (e.g., selfing) are described in U.S. Pat. No. 5,518,801, issued May 21, 1996 to Chappell et al.; U.S. Pat. No. 5,650,214, issued on Jul. 22, 1997 to Anderson et al.; and U.S. Pat. No. 6,114,263, issued Sep. 5, 2000 to Benson, et al.; U.S. patent application Ser. No. 09/669,329, filed Sep. 25, 2000 by Anderson et al.; all are incorporated herein by reference.

Ring-rolling process has the effect of elongating the absorbent structure, thereby partially disentangling them. Typically, the ring-rolling process also decreases the regional density and increases softness as well as absorptive capacity. Specifically, ring-rolling process takes advantage of the limited elasticity of the fibers in the web such that under the stretching forces applied by the teeth of the rolls, the web is partially broken up (i.e., partially disentangled). When the ring-rolling process is applied to a fibrous web structure made of relatively non-stretchable fibers such as rayon and other cellulosic fibers, a higher degree of web break-up occurs, resulting in more extensive decrease in regional fiber density, thus, more extensive mechanical weakening. Such mechanically weakened regions are susceptible to break-up under the pressure of the flushing devices, resulting in good flush dispersibility. Furthermore, the extent of the mechanical weakening in these fibrous webs of low extensibility are typically not achieved by traditional ring-rolled webs made of more extensible materials, such as polyolefins.

In order for the product to be dispersible upon flushing, the region of weakness typically comprises at least about 20%, preferably at least about 40%, more preferably at least about 50%, more preferably at least about 75%, and most preferably at least about 90% of the total surface area of the product.

Fibrous and non-fibrous absorbent structures can have regions of weakness incorporated therein to aid dispersibility. By regions of weakness what is meant is that the structure includes a regions such as but not limited to intermittent slits (i.e., discontinuous slits or perforations) or continuous slits, either of which extend at least partially, and optionally entirely, through the thickness of the absorbent structure. Processes such as ring rolling operate to either impart slits (generally continuous regions of weakness) or continuous regions of weakness characterized by partially separated fibers, wherein in the latter case the web is stretched during ring rolling to reduce density of the fibers in the stretched region.

In one preferred embodiment, the regions of weakness extend more than 50% through the thickness of the absorbent structure, optionally through the entire thickness of the absorbent structure. Such regions of weakness are in the form of continuous slits or discontinuous perforations or slits. Regions of weakness may also be formed (e.g., by cutting) into geometric or decorative shapes. Nonlimiting examples of these shapes include circles, squares, triangles, diamonds, animal shapes, floral or botanical shapes, cartoon figures.

Regions of weakness can be incorporated into the dispersible absorbent products by numerous techniques, as will be apparent to those skilled in the art. Without limitation, suitable ways to introduce regions of weakness include cutting or slitting the product with a blade; forming the absorbent structure initially with regions of weakness incorporated therein, such as by a pattern forming wire or web as used in paper making processes; ring-rolling, or variants thereof (e.g., selfing), the products under conditions wherein high tension points of the web break, or crack, during processing. Ring-rolling and selfing under these conditions depends upon the type of web material treated, pitch of the roll teeth, and degree of engagement of the opposing teeth of the rolls. In particular, it has been found that use of a high proportion of staple length or longer fibers with average fiber lengths of at least about 1 cm, preferably at least 2 cm, more preferably at least about 3 cm, are preferred for ring rolling processing wherein it is desired to introduce regions of weakness in the form of slits partially extending through the thickness of the absorbent structure, and especially for regions of weakness extending through at least 50% of the thickness or through the entire thickness of the absorbent structure.

In another preferred embodiment, regions of weakness are provided in the form of partially detangled fibers, or partially separated fibers, of lower density compared to the adjacent regions of higher tensile strength and density. Such products can be made by ring rolling or selfing as previously described. In particular it has been found that the use of long fibers, such as softwood fibers, or blends of such long fibers with short fibers, are preferred for ring rolling or selfing to make products with such partially detangled fibers in the form of regions of weakness.

Additionally, in accordance with the ring rolling or selfing process as further discussed below, incorporation of increased levels of water or other liquids in the web during the stretching/weakening step can further enhance the formation of reduced fiber density regions and minimize the formation of total break-up (resulting in slits, holes) of the fibrous web. Without being bound by theory, it is believed that the addition of water or other liquids may lower the coefficient of friction and enhance the slippage at the tensioning points between the fibrous web and the teeth of the rolls. Thus, the fibrous web suffers less abrasion and less breakage at the tensioning points. Consequently, the web is able to go through a process with a deeper engagement of the teeth. The resulting web has a more pronounced texture on its surface, which enhances softness, cloth-like feel to satisfy consumer preference and improves absorbency to satisfy functional requirement of the product. In general, it is preferred to include from about 0.0001 ml/square cm to about 0.004 ml water/square cm web surface during ring rolling for products desired to have regions of weakness in the form of low density regions of partially detangled fibers.

Figure 3:
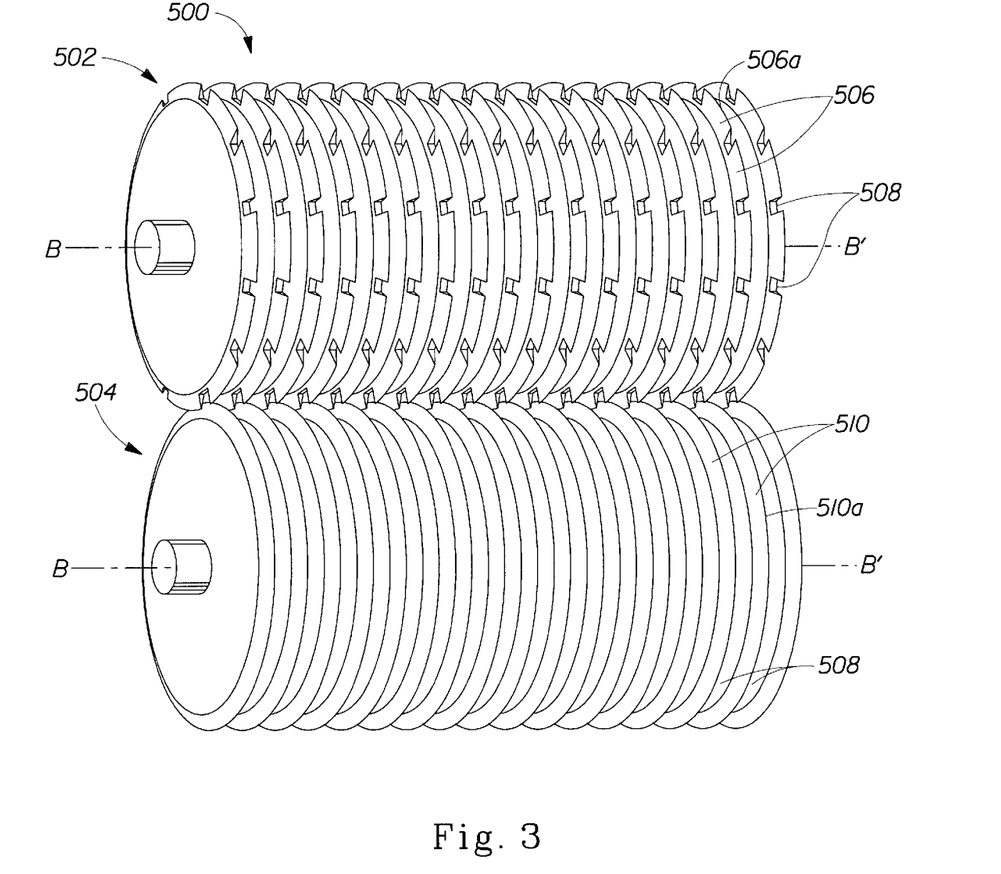
FIG. 3 shows a set of selfing rolls useful for manufacture of dispersible absorbent products of the present invention.

Referring now to FIG. 3, shown is a pair of preferred selfing rolls 500 having upper roll 502 and lower roll 504, which are suitable for mechanically weakening a fibrous web according to the present invention. Roll 502 has circular rows of teeth 506 with ridge lines 506a extending perpendicularly to the longitudinal axis of the roll B–B'. The rows of teeth 506 have notches 508, which impart the non-mechanically weakened regions. Notches 508 are optional features of the process and products of the present invention. Notches can create a pattern or texture in the finished absorbent structure. As shown in FIG. 3, lower roll 504 has rows of teeth 510 having ridge lines 510a extending perpendicularly to the longitudinal axis of the roll B–B' that do not have notches. Rolls 502 and 504 are aligned during use such that rows of teeth 506 are aligned approximately mid-point between rows of teeth 510.

Specific processing parameters can vary widely according to the specific materials utilized and degree of mechanical weakening desired. Processing conditions that can be used are described, for example in the selfing references discussed above and incorporated herein by reference. For preferred embodiments of the present invention, the spacing between rows of teeth in the B–B' direction is from about 0.02 inches (about 0.05 cm) to about 0.25 inches (about 1.25 cm), more preferably from about 0.04 (about 0.1 cm) inches to about 0.20 (about 0.51 cm) inches, more preferably from about 0.06 (about 0.15 cm) inches to about 0.15 inches (about 0.38 cm); most preferably about 0.1 (about 0.25 cm) inches; depth of the teeth is from about 0.08 inches (about 0.20 cm) to about 0.25 inches (about 0.64 cm), preferably from about 0.08 (about 0.20 cm) inches to about 0.18 inches (about 0.46 cm); pitch of the teeth is sufficient in view of the web thickness and other roll dimensions such that the web is not pinched between the teeth during processing.; and degree of engagement between teeth of the opposing rolls is from about 0.020 inches (about 0.005 cm) to about 0.20 inches (about 0.05 cm), preferably from about 0.04 inches (about 0.1 cm) to about 0.15 inches (about 0.38 cm), and most preferably from about 0.06 inches (about 0.15 cm) to about 0.1 inches (about 0.25 cm). The above parameters are preferred however are not meant to exclude selection of lower or higher values for use in making products otherwise in accordance with the present invention.

Figure 2:
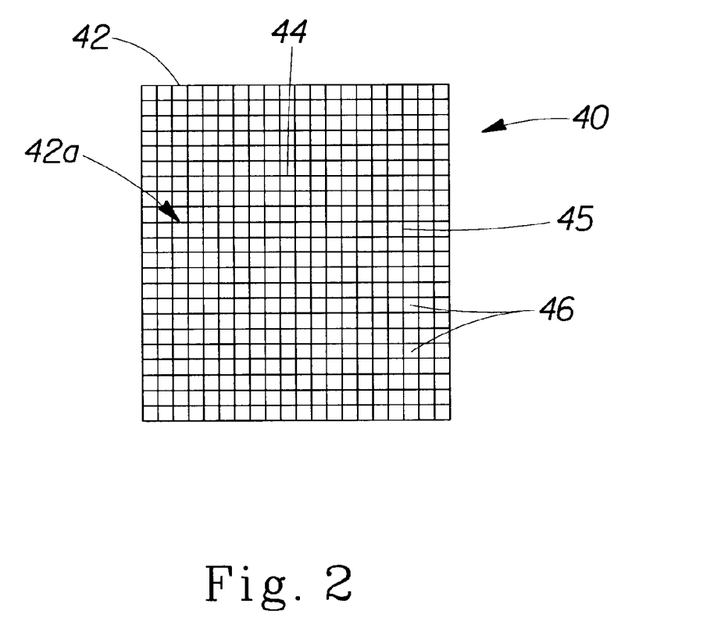
FIG. 2 shows a top planar view of an alternate embodiment of a dispersible absorbent product of the present invention.

Referring to FIG. 2, dispersible absorbent product 40 has a web structure 42 having top surface 42a with regions of weakness incorporated therein in a grid pattern of horizontal lines weakness 44 and vertical lines of weakness 45. In one embodiment, lines of weakness 44, 45 may be slits extending partially or entirely through the thickness of the structure 42. Such lines of weakness 44, 45 aid dispersibility of the plurality of discrete sections 46 of web structure 42. In another embodiment of the present invention, the web structure preferably, although not necessarily, is made from rayon, cellulosic fibers, polylactic acid fibers or a blend of these fibers such fibers or blend of fibers having an average fiber length of at least about 1 cm, more preferably at least about 2 cm, more preferably at least about 3 cm. The web structure may further comprise other cellulosic fibers including softwood fibers, especially chemically pulped softwood fibers, or a blend of softwood and hardwood fibers. In another embodiment, the web structures will contain at least about 25% softwood fibers, more preferably at least about 50% softwood fibers, most preferably at least about 80% softwood fibers. The relative proportions of types of wood fibers are as previously discussed.

In another embodiment corresponding to FIG. 2, the weaknesses 44, 45 may be continuous regions of partially disentangled fibers further characterized by being low density regions compared to the adjacent regions of non-mechanically weakened regions of fibers. Such regions of weakness 44, 45 aid in rapid dispersing of the product into individual fibers, or small chunks, agglomerations, or sections of fibers, or a combination thereof. Alternately the web structure can be considered as having a plurality of weakened regions disposed in a pattern (random or, in this specific embodiment, non-random) separated by non-weakened regions.

Figure 4:
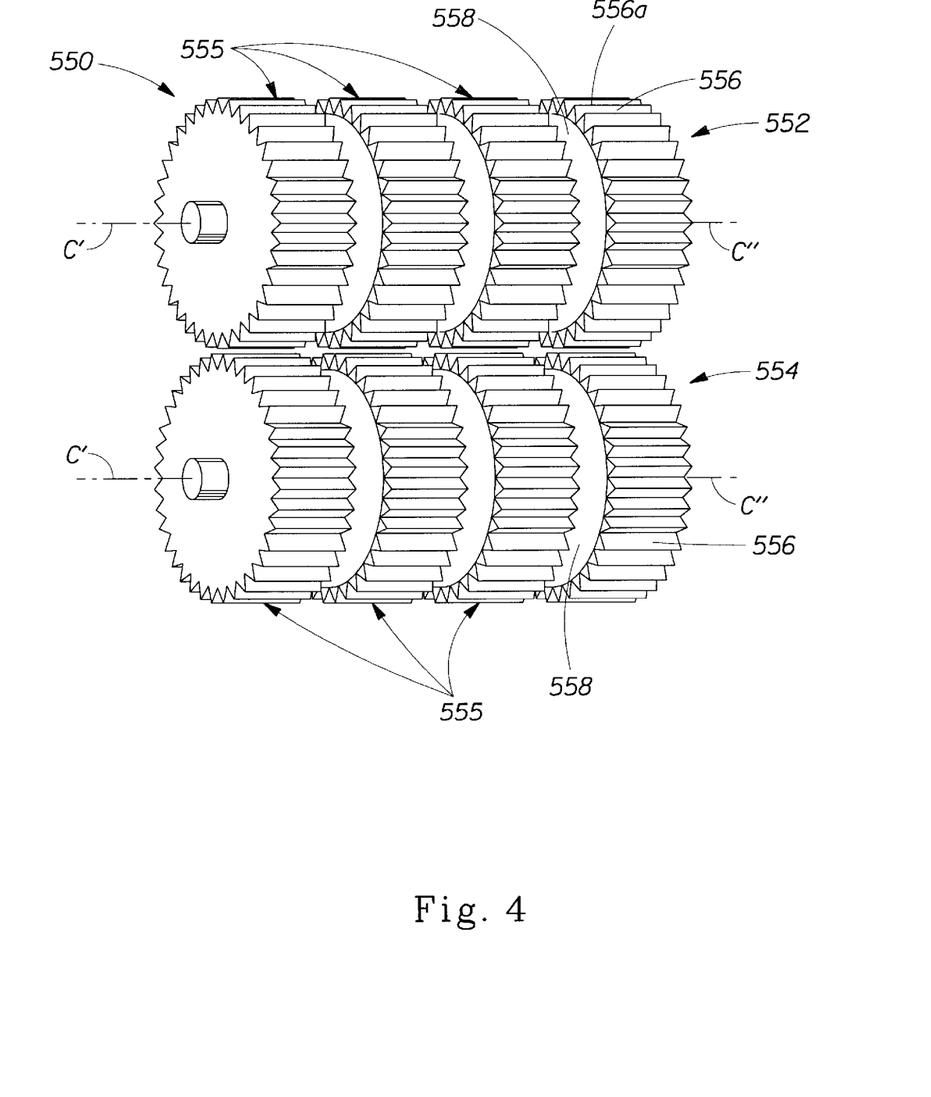
FIG. 4 shows a set of ring rolls useful for manufacture of dispersible absorbent products of the present invention.

Referring to FIG. 4, shown is a set of rolls 550 having upper roll 552 and lower roll 554, each with rows 555 of teeth 556 which cylindrically extend around the circumference of the rolls 552, 554, about axis C'–C''. Rows 555 of teeth 556 are separated by inactive grooves 558. Teeth 556 have ridge lines 556a which extend in a direction parallel to the axis C'–C''. Grooves 558 are optional and not essential for purposes of this invention. Optionally, teeth 556 can extend continuously along the width of the roll without grooves or other interruption to the teeth 556 or teeth ridge lines 556a. Rolls 550 can have the same range of teeth spacing, depth, and degree of engagement during use as described above.

In a preferred process for making dispersible absorbent products of the present invention, the absorbent structure is weakened by at least two sets of selfing rolls wherein one set of selfing rolls ring has teeth extending in a direction perpendicular to the longitudinal axis of the roll, such as shown in FIG. 3, and another set of selfing rolls has teeth extending in the direction parallel to the longitudinal axis of the roll, such as shown in FIG. 4.

Figure 1:
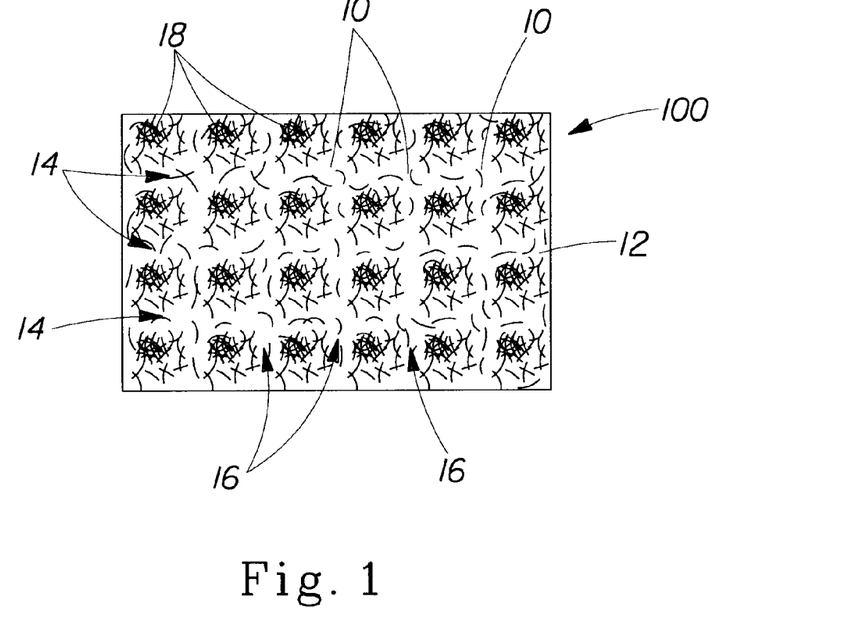
FIG. 1 shows a top planar view of a dispersible absorbent product of the present invention.

Each ring-rolling or selfing step of the present invention imparts regions of weakness in the dispersible absorbent product in a direction parallel with the teeth of the rolls. Thus, by using rolls that impart a plurality of perpendicular regions of weakness (i.e., a first set of regions of weakness in a horizontal direction and a perpendicular set of regions of weakness in a vertical direction, such as shown in FIGS. 1 and 2), a web structure having a grid pattern of regions of weakness can be provided.

In the preferred process for making the product as shown in FIG. 2, the second set of selfing rolls are as shown in FIG. 4 except with ridge lines of teeth that extend continuously along the axis of the selfing roll, i.e., without being separated into separate rows of teeth.

Noncontinuous regions of weakness can be provided by selfing with rolls having a plurality of notches along the perimeter of the teeth. Such notched teeth can be used for stretching the web in one direction or a plurality of directions upon the web structure, for example the second application of rolls being perpendicular to the first. Further combinations of notched teeth and non-notched teeth can be used for the rolls. Further, the teeth during any specific stretching step can include a combination of notched and non-notched teeth.

Other methods may be used for stretching and weakening the web including, but not limited to, tentering or tensioning. Tensioning process may be performed via differential roll speeds. For example, the take-up roll may be operated at a higher speed than the feed roll and/or the forming roll, thus, subjecting the web to a tensioning force in the machine direction. Whereas cutting, ring rolling and modified ring rolling processes create regional weaknesses, tentering and tensioning processes tend to create more global weakening of the web (i.e., the resulting web is substantially homogeneously weakened). In this aspect, the global weakening processes are more suitable as a secondary processes, after the web has been partially or substantially weakened by a primary weakening process, which creates regional weaknesses in the web. Thus, cutting, ring rolling and modified ring rolling (e.g., selfing) are primary weakening processes and tensioning and tentering are secondary weakening processes.

Figure 5:
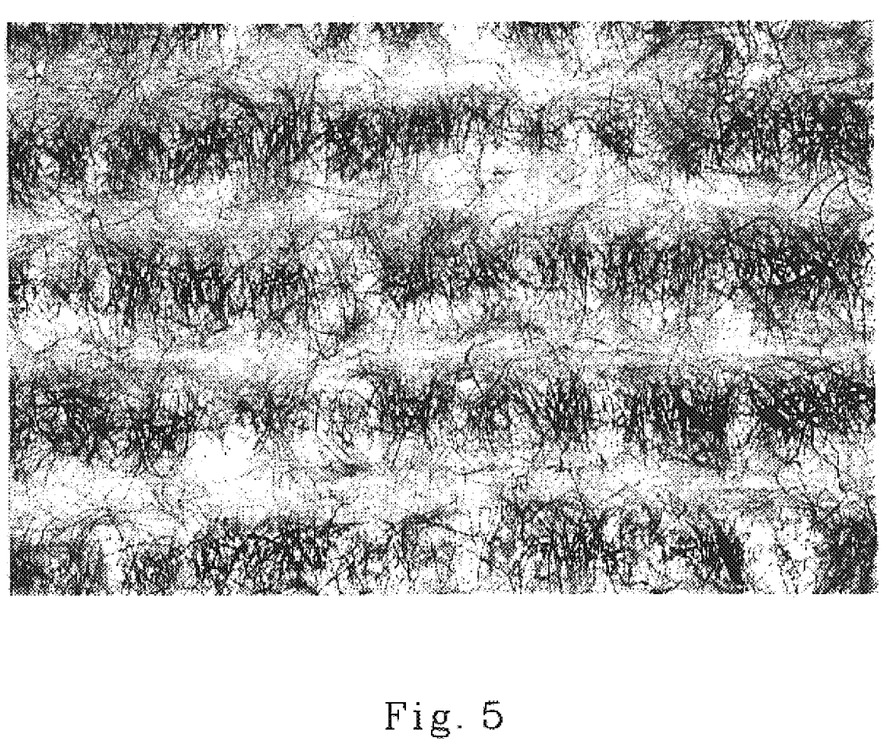
FIG. 5 is a 4× magnified photograph showing a top plane view of an embodiment of the present invention.
Figure 6:
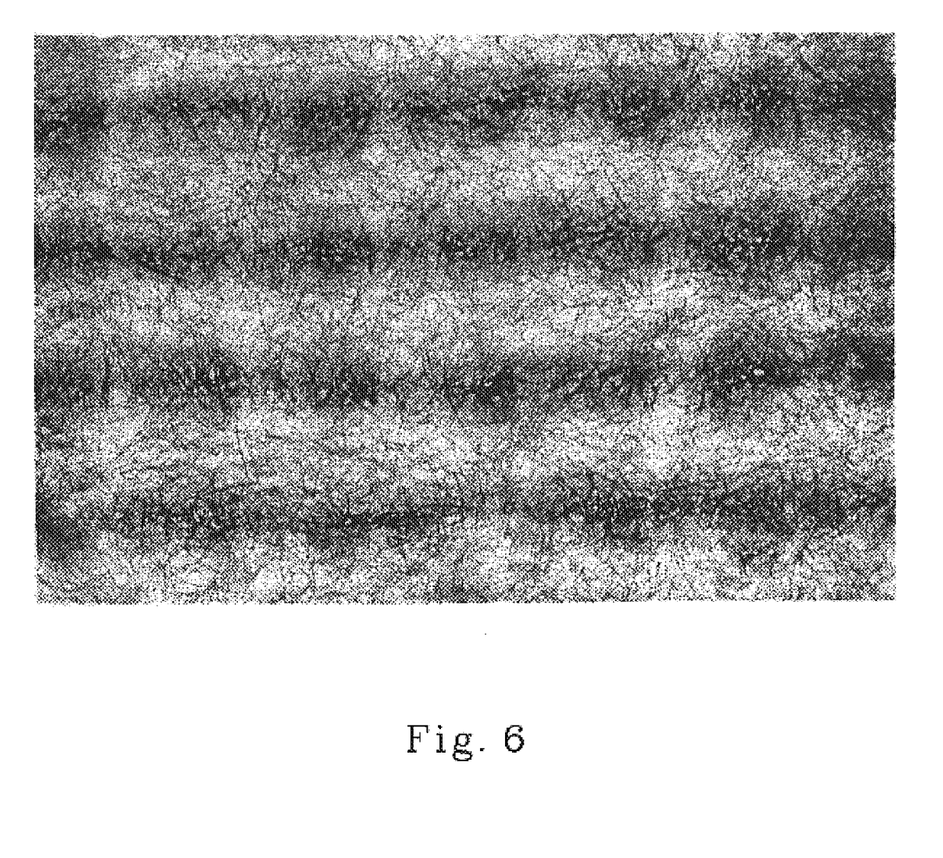
FIG. 6 is a 4× magnified photograph showing a bottom plane view of the product of FIG. 5.

FIGS. 5 and 6 are photographs exemplifying a preferred embodiment of the present invention that can be made by selfing a dispersible absorbent product in two directions, one direction perpendicular to the other, to form a pattern of regions of weakness that are parallel regions of partially detangled fibers (shown in FIGS. 5 and 6 as light colored parallel regions running horizontally across the photographs). Less distinct but still observable are a series of parallel, vertical regions of partially detangled fibers, also appearing as light colored regions. FIG. 5 shows a top planar view. FIG. 6 shows a bottom planar view. The darker regions correspond to portions of the absorbent structure that are not partially detangled by the selfing steps. The horizontal regions of weakness in FIGS. 5 and 6 would generally be formed by the second of the two, sequential selfing steps, while the less prominently observable vertical regions of weakness would generally be formed by the first of the selfing steps.

FIG. 1 is a drawing showing a top planar view of the preferred embodiment of an dispersible absorbent product 100, such as the type of product shown in FIGS. 5 and 6, having a fibrous web structure 12, with non-detangled regions 18 separated by horizontal regions of partially detangled fibers 14 and vertical regions of partially detangled fibers 16. The intersection regions 10 of the horizontal and vertical regions of partially detangled fibers 14, 16 will as a result of the two selfing steps be partially disentangled in both horizontal and vertical directions. Dispersible absorbent products as shown in FIG. 1 can be made using softwood fibers or other relatively long fibers (e.g., rayon), or blends of such long fiber types with hardwood fibers. In one embodiment, the fibrous web is made of 100% rayon. In another embodiment, the fibrous web is made of a blend comprising 75% wood pulp, 13% rayon and 12% latex binder (e.g., polyvinylacetate latex, acrylic copolymer latex, styrene-butadiene copolymer latex).

The products of the present invention can be used for a wide variety of purposes including but not limited to: toilet paper (e.g., for absorbing residual urine or other bodily fluids, for wiping residual bowel movement away from the body); wipes or like products for cleaning various bodily parts such as the anus, under-arms, neck, hand, feet, and/or face; household and hard surface cleaning wipes such as glass cleaners, kitchen cleaning, furniture cleaning, bathroom cleaning; industrial cleaning and fluid absorption products including any hard surface cleaning applications as well as chemical spill; personal care applications such as skin and facial cleaning; and application or removal of cosmetics, conditioners and/or health care actives to the skin; cleaning and/or wiping of clothes and textiles; baby care products such as bibs, and diapers; and health care products such as bandages.

Products hereof can be in a variety of shapes and sizes. The preferred products will be in the form of sheets. Such sheets can further be in a variety of shapes and sizes, and further can be in the form of semi-enclosed products, such as mitts or gloves, having an exterior comprising the absorbent sheet of the present invention, an interior region, and an opening through which a hand, finger, or body appendage or device may be inserted. Such semi-enclosed products can be made by attaching two parallel sheets to one another at the edges, such as by adhesives, while allowing at least one section of the edges to remain non-adhered, thereby providing an opening through which appendages or devices may be inserted.

Suitable compositions for the pre-moistened products may include, without limitation, simple liquids such as water, lower alcohols (such as methanol, ethanol, propanol), humectants (such as glycerin or propylene glycol), film forming agents (such as mineral oil or silicones), and combinations thereof. Suitable compositions may also include, without limitation, absorbent polymeric gelling materials (such as partially cross-linked polyacrylic acids/acrylates or other superabsorbent gelling materials generally found in absorbent articles), anti-bacterials, fragrances, skin conditioning agents, skin or facial cleansing agents, odor absorbing agents (e.g., cyclodextrins, alumina, silica, carbons), household or hard surface cleaning agents, preservatives and dyes. Nonlimiting examples of suitable compositions are described in U.S. Pat. Nos. 4,575,891; 4,917,823; 4,941,995; 5,525,345; 5,585,104; 5,643,588; 5,645,825; 5,648,083; 5,686,088; 5,720,966; 5,726,139; 5,871,762; 5,932,527; 5,965,115; 6,063,397; 6,093,410; 6,153,209; 6,183,763; and U.S. patent application Ser. No. 09/148,540; all are incorporated herein by reference.

In preparing the pre-moistened embodiments of the present invention, a composition suitable for the intended use is applied to at least one surface of the substrate web. The composition can be applied at any time during the manufacture of the product. Preferably, the composition is applied to the web after the mechanical weakening of the web. Any variety of application methods that evenly distribute compositions having a fluid or semi-solid consistency can be used. Suitable methods include spraying, dipping, printing, (e.g., flexographic printing), coating (e.g., gravure coating or flood coating), extrusion coating or combinations of these application techniques.

The composition may be applied uniformly or non-uniformly onto either or both surfaces of the product. The composition may also be applied in a pattern (i.e., stripes, boxes, dots, spirals, etc.). By non-uniform it is meant that, for example, the amount, pattern of distribution, etc., of the composition can vary over the surface of the substrate. In one embodiment, some of the surface of the substrate can have greater or lesser amounts of composition, including portions of the surface that do not have any composition on it. The composition may be applied in an amount of from about 0.5 g/g to 10 g/g, preferably from 1.0 g/g to 5 g/g, most preferably from 2 g/g to 4 g/g, based on the weight of the substrate web.

Test Methods

Flush Dispersibility Test

This test simulates the disposal conditions a product experience in a toilet.

Equipment

The system consists of the US standard toilet (1.6 gallons/flush) connected to 59 feet of 4" ID drainpipe. The US standard toilet represents the worst case for clogging in the trap. The drainline has 90° elbows about every 15 feet such that it is configured into a square. The system is configured with a 2% drop in elevation between the commode and the end of the drainline. Approximately 15 feet from the pipe's terminal, the drainline is partially occluded (about 10% of the total cross-sectional area) by a mass of cement. This simulates a drainline obstruction and is used to measure a product's potential to accumulate, persist and cause clogging in partially occluded drainpipes.

Test Products/Loading

A test product is placed in the commode and held for 10 seconds. Next the system is flushed. After passage through the drainline, the product is retrieved, laid flat and given a dispersion rating (see below.) The test is repeated to allow for 10 product flushes.

Dispersion Rating

Upon retrieval from the drainline sieve, each product is rated for dispersion per the following scale:

| Rating | Description |
|---|---|
| 0 | No visible sign of weakness or dispersion is evident. |
| 1 | Product contains voids that are the result of fiber separation. |
| 2 | Product contains multiple holes or tears equivalent to 20% of surface area. |
| 3 | Product is retrieved in multiple pieces, or product contains holes which produce voids in greater than 20% of the product surface area. |

Ten product flushes must achieve an average dispersion rating of at least '2'. Most preferred is a dispersion rating of '3'.

Tensile Test

A commercial tensile tester from Instron Engineering Corp., Canton, Mass. or SINTECH-MTS Systems Corporation, Eden Prairie, Minn. may be used for this test. For CD tensile properties, the films or laminates are cut into 1" wide in MD (the machine direction of the film/laminate) by 2" long in CD (the cross machine direction which is at a 90° angle from MD) specimens. For MD tensile properties, the orientation of the film/laminate is rotated 90°. The instrument is interfaced with a computer for controlling the test speed and other test parameters, and for collecting, calculating and reporting the data. These tensile properties are measured at room temperature (about 20° C.). The procedure is as follows:

1. choose appropriate jaws and load cell for the test; the jaws should be wide enough to fit the sample, typically 1" wide jaws are used; the load cells is chosen so that the tensile response from the sample tested will be within the capacity of the load cell used, typically a 50 lb load cell is used;
2. calibrate the instrument according to the manufacture's instructions;
3. set the gauge length at 2";
4. place the sample in the flat surface of the jaws according to the manufacturer's instructions;
5. set the cross head speed at a constant speed of 20"/min;
6. start the test and collect data simultaneously; and
7. calculate and report tensile properties; the average result of a set of five sample is reported.

Rate of Dispersibility

Rate of Dispersibility is determined according to a modified Japanese Industrial Standard (JIS) test P4501-1993. An 800 ml cylindrical graduated Griffin beaker (6.3 cm by 15.2 cm, such as VWR Scientific Products, Catalogue #13910-267, 1997/1998) with 300 ml water deionized (DI) water at 23 degrees C. is equipped with a 35 mm diameter magnetic starhead stir disk (12 mm maximum thickness, starhead protrusions extending from both sides, such as available from VWR Scientific Products, catalogue #58948-568, 97/98, or equivalent), and placed on a magnetic stir plate set to rotate the stir disk at 600 revolutions per minute (rpm).

A 0.38 g sample of absorbent product is pre-conditioned at 20 degrees C. (+/-5 degrees C.) and 65% Relative Humidity (+/-5%) until equilibrium. In the event that the product to be tested is less than 0.38 g, then multiple products or fractions of multiple products are used to increase the total weight to 0.38 g. In the event that the product to be tested is larger than 0.38 g, then product size is reduced such that a 0.38 g portion of the product is tested. The product sample tested according to the present test should have a total exterior surface area of at least 20 $cm^2$. If the total exterior surface area of a product sample that has been reduced to 0.38 g is less than 20 $cm^2$, then a larger sample of the product should be used for the present test such that the total surface area is 20 $cm^2$.

The sample is dropped into the center of the vortex caused by the stirring, which causes stir bar rotational rate to decrease, and a stopwatch is simultaneously started. The time in seconds for the stir bar to increase in rotational rate until it reaches 540 rpm is recorded as the Rate of Dispersibility. If addition of the sample to the beaker causes the stir disk to be moved off center from its natural axis of rotation or if it ceases rotating, the test run is invalid and should be repeated with a new sample of product.

While particular embodiments of the present invention have been illustrated and described, it would be obvious to those skilled in the art that various other changes and modifications can be made without departing from the spirit and scope of the invention.

What is claimed is:

1. A dispersible, pre-moistened absorbent sheet product consisting essentially of a fibrous, mechanically weakened web having at least one mechanically wakened region, wherein a liquid or a composition is applied to at least one surface of the mechanically weakened web, the web comprises less than about 5 wt % of a wet strength resin, and wherein the product is flushable.

2. The dispersible absorbent product of claim 1, wherein the mechanically weakened web has a reduction in tensile strength of at least about 50% based on me tensile strength of the unweakened web.

3. The dispersible absorbent product of claim 2 wherein the mechanically weakened web has a reduction in tensile strength of at least about 70% based on the tensile strength of the unweakened web.

4. The dispersible absorbent product of claim 3, wherein lie weakened web has a reduction in tensile strength of at least about 80% based on the tensile strength of the unweakened web.

5. The dispersible absorbent product of claim 1, wherein the mechanically weakened web has a residual tensile strength, after being mechanically weakened, of at least about 70 g/in (28 g/cm).

6. The dispersible absorbent product of claim 5, wherein the mechanically weakened web has a residual tensile strength, after being mechanically weakened, of at least about 150 g/in (60 g/cm).

7. The dispersible absorbent product of claim 1, wherein the mechanically weakened web has a residual tensile strength, after being mechanically weakened, of at least about 250 g/in (100 g/cm).

8. The dispersible absorbent product of claim 1, wherein the web comprises fibers having an average length of at least about 1 cm.

9. The dispersible absorbent product of claims 1, wherein the web comprises at least tout 50% by weight cellulosic fibers.

10. The dispersible absorbent product of claim 1, wherein die web further comprises polymers selected from the group consisting of poly(lactic acids), polycaprolactones, aliphatic polyesters, aliphatic polyalkylene succinate polymers, polyalkylene succinate adipate copolymers, aliphatic-aromatic copolyesters, polyesteramides, polyhydroxyalkoates and copolymers, cellulose derivatives, polyalkylene oxides, polyvinyl alcohol and copolymers, other vinyl polymers, starch, nylon copolymers, acrylic acid copolymers, polyethylene glycol, and mixtures thereof.

11. The dispersible absorbent product of claim 1, wherein the web contains at least about 50% rayon, by weight.

12. The dispersible absorbent product of claim 11, wherein the web comprises at least about 70% rayon, by weight.

13. The dispersible absorbent product of claim 12, wherein the web comprises at least about 80% rayon, by weight.

14. The dispersible absorbent product of claim 1, wherein the weight of the liquid or the composition is from about 50% to about 300% of the weight of the web.

15. The dispersible absorbent product of claim 1, wherein the mechanically weakened region comprises partially disentangled fibers.

16. The dispersible absorbent product of claim 1, wherein the mechanically weakened region comprises cut fibers.

17. The dispersible absorbent product of claim 1, wherein the product has a basis weight of from about 50 g/m$^2$ to about 300 g/m$^2$.

18. The dispersible absorbent product of claim 1, wherein the product is biodegradable.

19. The dispersible absorbent product of claim 1, wherein the web is mechanically weakened by a process selected from the group consisting of perforating, cutting, slitting, ring rolling, selfing, tentering or tensioning by differential roller speeds and combinations thereof.

20. A method at making a dispersible, pre-moistened absorbent sheet product, comprising:
   providing an unweakened fibrous web;
   mechanically weakening the fibrous web in at least one region whereby the web becomes a mechanically weakened web;
   applying less than 5 wt % of a wet strength resin to said web; and
   applying a liquid or a composition to at least one surface of the web.

21. The method of claim 20, wherein the mechanically weakened web has a reduction in tensile strength of at least about 50% based on the tensile strength of the unweakened web.

22. The method of claim 21, wherein the mechanically weakened web has a reduction in tensile strength of at least about 70% based on the tensile strength of the unweakened web.

23. The method of claim 22, wherein the mechanically weakened web has a reduction in tensile strength of at least about 80% based on the tensile strength of the unweakened web.

24. The method of claim 20, wherein the mechanically weakened web has a residual tensile strength, after being mechanically weakened, of at least about 70 g/in (28 g/cm).

25. The method of claim 24, wherein the mechanically weakened web has a residual tensile strength, after being mechanically weakened, of at least about 150 g/in (60 g/cm).

26. The method of claim 25, wherein the mechanically weakened web has a residual tensile strength, after being mechanically weakened, of at least about 250 g/in (100 g/cm).

27. The method of claim 20, wherein the mechanical weakening is performed by partially disentangling at least a portion of the fibers.

28. The method of claim 20, wherein the mechanical weakening is performed by cutting at least a portion of the fibers.

29. The method of claim 20, wherein the fibrous web is mechanically weakened by a process selected from the group consisting of perforating, cutting, slitting, ring rolling, selfing, tentering or tensioning by differential roller speeds and combinations thereof.

30. The method of claim 20, wherein the web comprises at least about 50% by weight cellulosic fibers.

31. The method of claims 30, wherein a liquid or a composition is applied to at least one surface of the web, the weight of the liquid or the composition is hum about 50% to about 300% of the weight of the web.

32. The method of claim 30, wherein the web contains at least about 50% rayon, by weight.

33. The method of claim 20, wherein the web further comprises polymers selected from the group consisting of poly(lactic acids), polycaprolactones, aliphatic polyesters, aliphatic polyalkylene succinate polymers, polyalkylene succinate adipate copolymers, aliphatic-aromatic copolyesters, polyesteramides, polyhydroxyalkoates and copolymers, cellulose derivatives, polyalkylene oxides, polyvinyl alcohol and copolymers, other vinyl polymers, starch, nylon copolymers, acrylic acid copolymers, polyethylene glycol, and mixtures thereof.

* * * * *